United States Patent [19]

Shyu

[11] Patent Number: 4,770,189

[45] Date of Patent: Sep. 13, 1988

[54] REAL TIME MULTITASK ELECTRONIC STETHOSCOPY SYSTEM

[75] Inventor: Jia-Ming Shyu, Hsien, Taiwan

[73] Assignee: Industrial Technology Research Institute, Taiwan, Taiwan

[21] Appl. No.: 902,652

[22] Filed: Sep. 2, 1986

[51] Int. Cl.$^4$ .............................................. A61B 7/00
[52] U.S. Cl. .................................... 128/773; 128/903; 381/67
[58] Field of Search .............. 128/773, 903, 696, 715; 381/67; 434/262, 266

[56] References Cited

U.S. PATENT DOCUMENTS

| | | | |
|---|---|---|---|
| 3,724,455 | 4/1973 | Unger | 128/903 |
| 3,832,994 | 9/1974 | Bicher et al. | 128/705 |
| 4,170,717 | 10/1979 | Walshe | 381/67 |
| 4,534,058 | 8/1985 | Hower | 381/67 |
| 4,598,417 | 7/1986 | Deno | 381/67 |
| 4,618,986 | 10/1986 | Hower | 381/67 |

FOREIGN PATENT DOCUMENTS 65295  1/1969  Fed. Rep. of Germany ...... 128/903

*Primary Examiner*—Edward M. Coven
*Assistant Examiner*—John P. Lacyk
*Attorney, Agent, or Firm*—Cushman, Darby & Cushman

[57] ABSTRACT

A diagnostic system comprising one or more stethoscopes and a diagnostic unit. Each stethoscope is used to pick up a sound, which is then transmitted in radio form via an antenna after amplification through an electric/audio transducer. The sound, after being received by the diagnostic unit, is compared in a computer for diagnosis of the symptoms. The result of the diagnosis is then transmitted through an antenna and received by the stethoscope for reference by its user.

3 Claims, 3 Drawing Sheets

REAL TIME MULTITASK ELECTRONIC STETHOSCOPY SYSTEM

BACKGROUND OF THE INVENTION

The present invention relates to a stethoscopy system, particularly to a real-time multitask electronic stethoscopy system including one or more stethoscopes and a microcomputer for processing of the signal picked up by the stethoscopes so that signals from several stethoscopes may be compared for diagnostic purposes.

Generally, a patient's or machine's health condition can be determined through the detection of the frequency of a sound and the amplitude and the periodic features of a fluid (such a blood, air, water ...) flow or solid movement (linear, rotation, or vibration) in the patient's body (or machine) by experience and inference, whereby the cause, place and the presence of a normal or abnormal condition can be used for reference in therapy or repair. This method is called stethoscopy, the common manner of diagnosis used by medical man and maintenance engineer alike. Its principle is not hard to understand, but its practicality mainly depends upon experiences of the user. Therefore, there are numerous defects with prior art stethoscopy techniques, such as:

(1) Diagnosis will be difficult if the user has a hearing defect or if the signal from the stethoscope is too small.

(2) Accuracy of diagnosis is doubtful, for there is no reference signal for comparison while listening; instead, comparison is made by the user subjectively.

(3) Accuracy of diagnosis is doubtful if the diagnosis is determined by an unexperienced user who does not have enough patterns of symptoms in his mind for comparison purposes.

(4) Using a stethoscope requires repeated practices and instructions by an experienced user, and the practices and instructions may cause in convenience to patients.

(5) A stethoscope is a professional tool, and the public, especially those who live in a place where transportation is not convenient and medical facilities are not sufficient, cannot use one for self-diagnosis.

(6) Even an experienced medical man cannot make a correct diagnosis for a symptom he has never experienced or a symptom with a very slight change of sound pattern. For example, a minor irregular hearbeat symptom is rather difficult to be detected even by an experienced doctor with a stethoscope.

(7) The inner or outer mechanical troubles may be detected using a stethoscope; however, an experienced stethoscopic technician is very difficult to obtain, if not impossible.

The prior art inventions or improvements of the stethoscope merely pertain to the technology of picking up the sound signal and converting the sound signal. In U.S. Pat. No. 4,528,690, for example, a simple combination of an electronic means and a sound-guiding tube is provided. Another U.S. Pat. No. 4,528,689 relates to a means, which can have a sound signal, via a microprocessor, elongated in time (i.e., converted it into a slower form) so as to facilitate the diagnosis operation. Other U.S. Patents such as U.S. Pat. Nos. 3,562,428; 3,846,585; 4,220,160 etc. utilize a sound/electric signal conversion means to have the sound signal processed through a filter(s), an amplifier(s) and a recorder, etc; however, the diagnosis results are still mainly dependent upon the experience and skills of the user. Thus, the aforesaid problems have not been solved yet.

SUMMARY OF THE INVENTION

The present invention relates to a solution of the above defects. It can record and store a lot of signal patterns that can be used by a number of persons simultaneously. It further comprises a micro-computer as an aid for diagnosis. In addition to its applications in the medical field (for human beings and animals), it can be used to diagnose machinery and structure as well.

The present invention particularly relates to a stethoscopy system, particularly a real time multitask electronic stethoscopy system comprising one or more stethoscopes and a micro-computer for transmission of a signal picked up by the stethoscope, signals received by other stethoscopes in the same system being compared with reference patterns in the computer for diagnostic purposes.

DETAILED DESCRIPTION

A detailed description is given below with reference to the attached drawings.

Figures 2, 3:
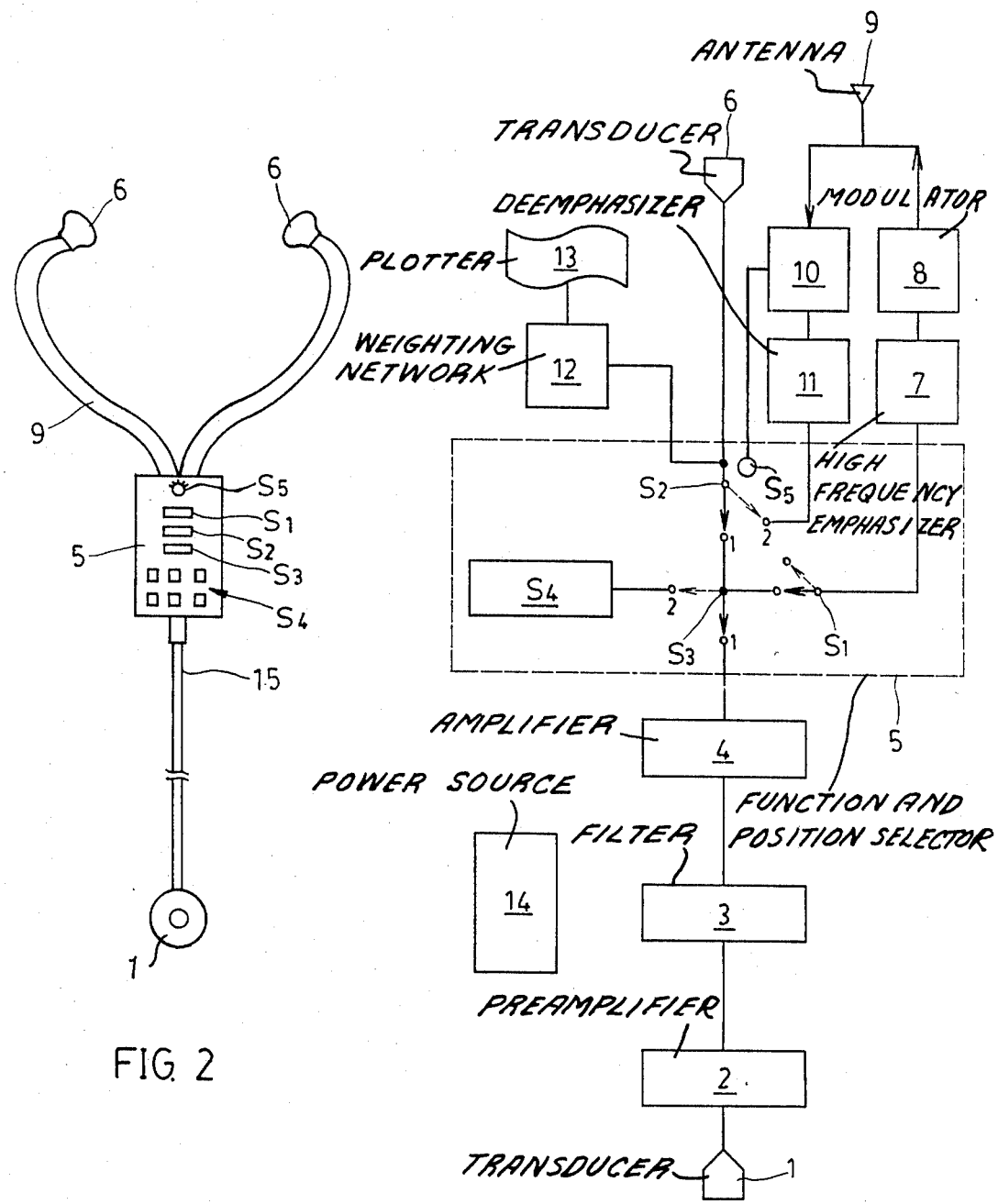
FIG. 2 illustrates the structure of a stethoscope according to the present invention.
FIG. 3 is a block diagram for the stethoscope according to the present invention.

As shown in FIGS. 2 and 3, the stethoscope according to the present invention comprises an audio/electric signal transducer (1), a preamplifier (2), a filter (3), a signal amplifier (4), a function and position selector (5), an electric/audio signal transducer (6), a high frequency emphasizer (7), a modulator (8), an antenna (9), a demodulator (10), a de-emphasizer (11), a weighting network (12), a plotter (13), a power source (14) and a flexible tube (15).

Figure 4:
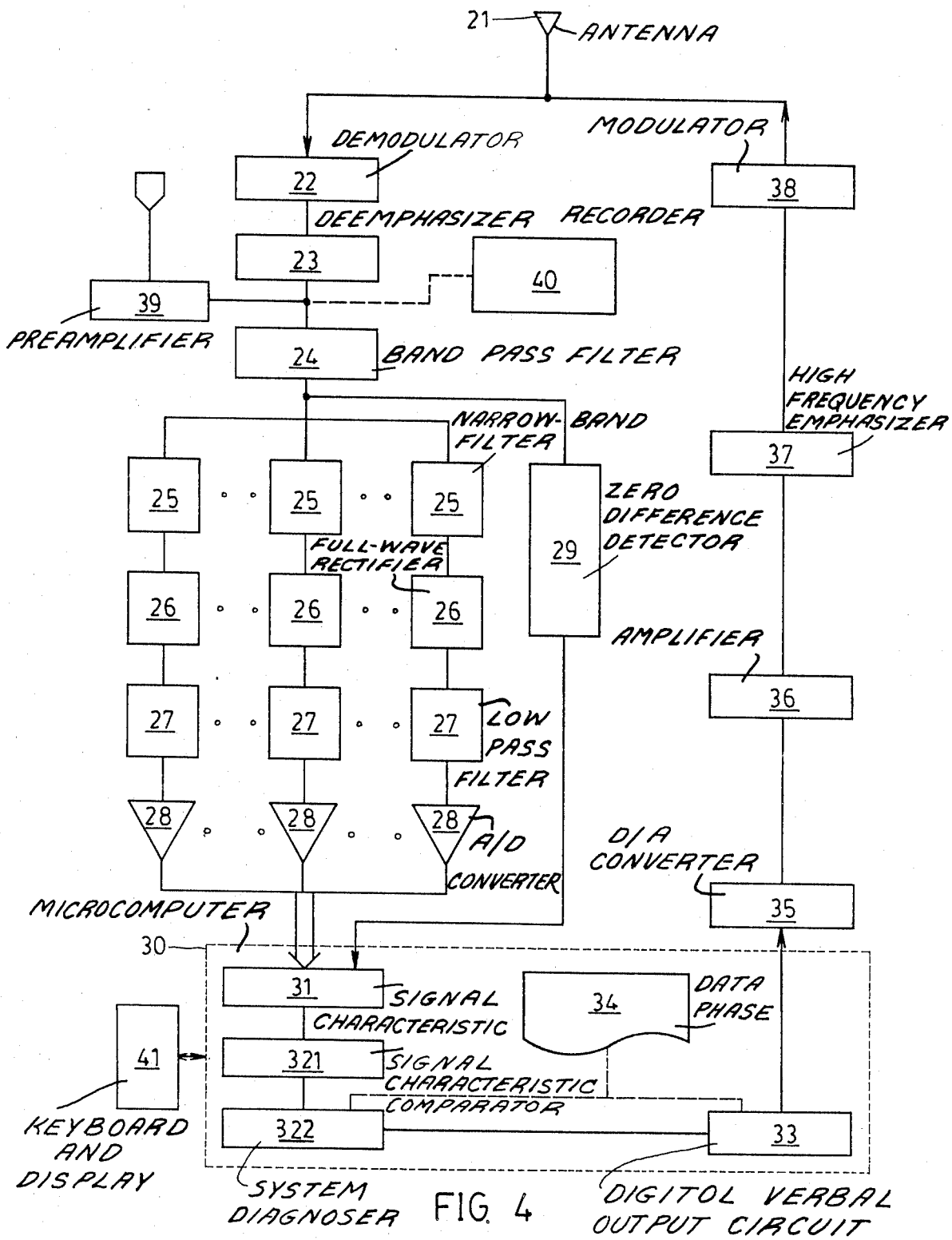
FIG. 4 is a block diagram for a diagnositc unit according to the present invention.

Referring now to FIG. 4, the diagnostic unit according to the present invention is shown, which comprises an antenna (21), a demodulator (22), a de-emphasizer (23), a band pass filter (24), a narrow-band filter (25), a full-wave rectifier (26), a low pass filter (27), an analog/digital converter (28), a zero difference detector (29), a microcomputer (30), a signal characteristic pickup (31), a signal characteristic comparator (321), a symptom diagnoser (322), a digital verbal output circuit (33), a data base (34), a digital/analog converter (35), an amplifier (36), a high frequency emphasizer (37), a modulator (38), a microphone and preamplifier (39), a recorder (40), a keyboard and display (41), etc.

The stethoscope elements function as will be described below.

The audio/electric signal transducer (1) converts sound into an electronic signal for further processing. A condenser microphone is preferable, for it is compact in size, and has appropriate sound sensitivity over a wide frequency response range with low noise.

The preamplifier (2) is an amplifier with high input impedance and a high gain and is used at the output of the microphone for impedance matching. A capacitor microphone, for example, can use an emitter follower for the first stage of amplification. The preamplifier is of a multi-stage amplification, and is placed as close to the microphone as possible to minimize noise interference. The amplifiers are connected with shield wires of low impedance and via the interior of the tube (15) to prevent noise interference.

In filter (3) the signal picked up by the microphone is filtered so as to filter out noise as much as possible before further amplification. The filter (3) may include a set of band pass filters which are used for removing the low and high frequencies and may also include a differential circuit used for differentiating the high frequency signal so as to remove a spike contained therein.

The signal amplifier (4) amplifies the treated sound signal, and the volume of its output can be adjusted by a variable resistor (VR) to fit individual preference.

The function and position selector (5) mainly comprises four selector switches (S1, S2, S3 and S4) and a modulation frequency tuning knob (S5).

Transmission selector switch (S1) is used to control the "on or off" state of a modulation transmission circuit. Upon turning on the transmission circuit, more persons can receive the signal simultaneously, and upon turning off the circuit, only the stethoscope that picks up the sound can receive the signal.

Receiving selector switch (S2) is used to select the source of sound. When in position 1, the microphone built in the stethoscope is the source of sound; and when in position 2, the sound comes from other stetoscopes in the system, i.e., the demodulation circuit has been turned on so that a signal from another stethoscope besides switch S1 is received.

Transmission signal selector switch (S3) is used to select the form of signal to be transmitted. When in position 1, the signal to be transmitted is the sound signal picked up by the microphone. When in position 2, on the other hand, the signal to be transmitted is the position signal selected with switch S4. When the switch (S3) is set at position 1, the power source to the position selection circuit is also turned off to minimize the power consumption.

Each stethoscope can generate two different signals which can be received by another stethoscope or computer in the system, i.e., the sound and the control signal of the position to be diagnosed, as controlled by the switch (S3). The sound picked up by the microphone is a compound signal composed of multiple frequencies. Therefore, a single frequency signal is used as the position signal in order to distinguish it from the compound sound. The position selector switch set S4 controls the transmission of this single frequency signal. Only one key can be pushed down at a time, and the resulting position control signal is used to control the operation of the diagnostic unit.

Modulation frequency selector switch (S5) selects from a variety of transmission frequencies for modulation for selecting the frequency desired.

The electric/audio transducer (6) comprises a pair of earphones for converting the electronic signal received and processed by the microphone into an audible signal.

The high frequency emphasizer (7) comprises a filter and an amplifier for emphasis of high frequency signals in order to enlarge the signal-to-noise ratio, and so as to minimize noise interference during radio transmission. The audible signal in the stethoscope thus not only can be heard by means of earphones, but also can be transmitted via a radio transmitter.

After high frequency emphasizing, the voltage signal is converted by modulator (8) into a radio frequency signal for radio transmission. The frequency of radio transmission can be the non-FM frequencies ranging from 78-90 MHz. A plurality of stethoscopes can be used for receiving and transmission of one frequency in one system, whereas several systems can be used simultaneously at different frequencies.

The antenna (9) is used to transmit and receive FM radio signals. A binaural metal pipe (9) (FIG. 2) can be used as an antenna for each stethoscope.

The demodulator (10) comprises a demodulation circuit to demodulate the received radio signal from the stethoscope or the computer in the system.

The emphasized signal is then de-emphasized by de-emphasizer (11) upon receiving in order to restore the signal to its original form and to improve the signal-to-noise ratio.

In addition to providing an output through earphones or the modulator, the waveform of sound can also be plotted into a pattern as an output signal by means of a plotter. Since a plotter has a long response time, however, it cannot receive a high frequency signal; therefore, the signal must be processed through a weighting network composed of a set of filters so as to give the output signal the same frequency response. The waveform of sound after being processed through the weighting network and being rectified, amplified and filtered can be used to drive the plotter (13) to draw a sound graph, such as a phonocardiogram, for reference in diagnosis.

The power source (14) can be mercury or other rechargeable battery, such as a Ni-Cd battery. A charger is provided for charging the battery when the stethoscope is not in use. The stethoscope thus may be incorporated with a power saving means, which is to be turned on when the earphone tubes are in use.

Figure 1:
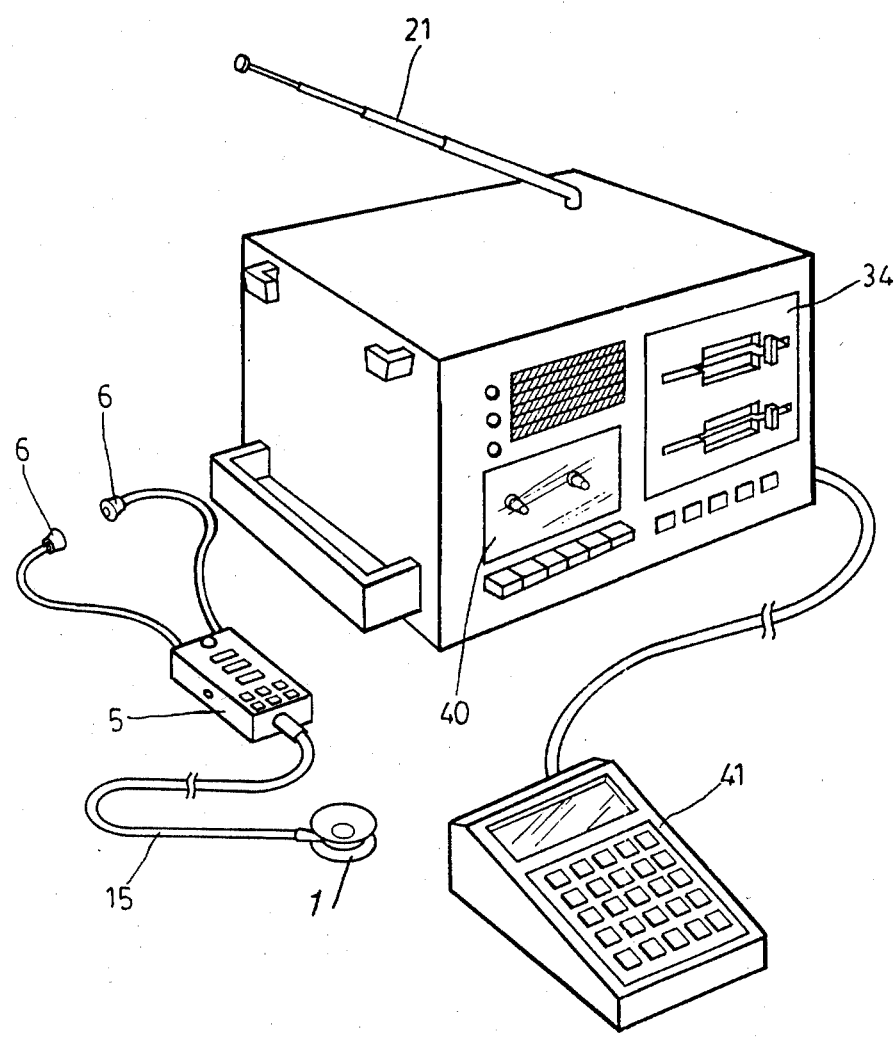
FIG. 1 is a perspective view illustrating a system according to the present invention.

The diagnostic unit of FIGS. 1 and 4 functions as will be described hereinafter.

An antenna (21) is used to receive a sound and position signal from the stethoscope and to transmit a symptom verbal signal to the stethoscope.

A demodulator (22) receives and demodulates the radio signal from the stethoscope.

A deemphasizer (23) then attenuates the high frequency emphasized signal from the stethoscope.

A band pass filter (24) responsive to the de-emphasized signal comprises an eight pole low pass filter and a three pole high pass filter connected in series so as to let the sounds of an audible frequency pass through while attenuating all other signals.

Narrow-band filters (25) extract different frequency components of the filtered sound and divide the sound signal into various bands so as to set up a pattern of the sound signal according to its characteristics. A plurality of narrow-band filters are used for the analysis after wide band filtration. Each narrow-band filter may comprise two two-pole voltage controlled voltage source (VCVS) filters that include multiple feedback loops, and the overall filter system may consist of from 5–32 band filters.

A full-wave rectifier (26) processes each narrow banded signal from the narrow-band filters to form respective d.c. signals.

A low pass filter (27) filters the d.c. signal from each full-wave rectifier to filter out the high frequency noise.

An analog/digital converter (28) then converts the analog signal into a digital signal for use by the microcomputer, and it also converts the continuous signals into the form of discrete parameters. Parameters from each band (filter) at a certain time can be expressed as follows:

$$A(t) = [X_1(t), X_2(t), \ldots X_n(t)],$$

wherein n is the number of bands.

The time sequence waveform, i.e., the waveform parameters set, can be described upon continuous collection of the parameters. If it is a position selector signal, for example, since it is a mono-frequency signal, only one certain element of $X_n(t)$ will be non-zero, and it can be determined as a position signal accordingly for further processing by the computer.

A zero difference detector (29) then detects the number of waveform changes to cross a reference line within a certain period in order to acquire the density of the basic sound waveform.

A micro-computer (30) comprises a signal characteristics extractor, a signal characteristics comparator, a symptom diagnoser, a data base, a digital verbal output circuit, a keyboard, etc.

The signal characteristics extractor (31), analysis of the frequency spectrum and zero difference detection are performed for determining the sound level (energy) and the basic waveform density and other parameter of the sound which are characteristic of the sound. The microcomputer is used, with appropriate software, to set up a pattern of the sound for further processing.

A signal characteristics comparator (321) provides basic criteria for determination of various symptoms of a normal sound, such as the first cardiachema, the second cardiachema, the interval between the first and second cardiachemas, etc., with the help of appropriate software as desired.

A symptom diagnoser (322) recognizes different patterns of detected sound which differ from the reference pattern whenever there is a symptom. The symptom diagnoser is used to diagnose occurrence of a symptom with appropriate software and reference data stored in the data base.

A digital voice output device (33) may be used to tell by voice the name of and information concerning a possible disease after the aforesaid diagnosis. Voice data of the name and other particulars of diseases can be stored in the computer via microphone and preamplifier, and by means of the aforesaid filter set and software, the parameters may be kept in the data base of the computer for future use.

A data base (34) contains patterns of sound for various diseases and the voice data of the disease names (causes). It can be put in a memory device in the form of a magnetic optical disk, and the diagnostic unit (321 and 322) functions with reference to data contained in the data base.

A digital/analog converter (35) and an amplifier (36) convert the digital voice data which is composed of the digital parameters. The converter is required to convert them into an analog voltage for regeneration of an audible signal, that is, the parameters are converted into a voltage waveform which is then amplified for transmission.

A frequency emphasizer (37) and a demodulator (38) convert the regenerated audible signals into a radio wave for transmitting the diagnostic data to the stethoscopes described above.

A microphone and a preamplifier (39) are used for inputting the audible data received and for amplification of these signals.

Since the sound is transmitted by radio, it can be received and recorded in recorder (40) with an FM receiver/recorder for re-listening and teaching purposes. The receiver/recorder can also be operated with a closed-circuit system.

A keyboard and a display (41) may be used for keying in and display of the diagnostic data.

In conclusion, the present invention is a real-time multitask electronic diagnosis system, which comprises one or more stethoscopes and a micro-computer for transmission of a signal so that the signal picked up by one stethoscope can be received by the other stethoscopes simultaneously. The micro-computer can also compare the signal with some reference signals to provide the user with a diagnosis reference. It is a system which is useful in recording, processing, accumulating and multiplex transmission of data to thereby improve the accuracy of diagnosis and to facilitate diagnosis.

I claim:

1. An electronic stethoscopy system comprising a plurality of stethoscopes and a remote unit which communicates with said plurality of stethoscopes, each stethoscope also communicating with each other stethoscope and including:

a pick-up circuit including a microphone for transforming detected sound into an electric signal, an amplifier for amplifying said electric signal and filters for removing noise in said electric signal;

transmitting and receiving circuits including an emphasizer receiving, via a first switch, the amplified and filtered signal from said pick-up circuit for emphasizing high frequencies, a modulator for modulating the emphasized signal for transmission, a demodulator for demodulating an input signal received from the remote unit or another stethoscope, and a deemphasizer for deemphasizing high frequencies in the demodulated signal; and a binaural earpiece having speakers selectively connected, via a second switch, to the amplified and filtered signal from said pick-up circuit or to the deemphasized signal from said receiving circuit, wherein the detected sound from one stethoscope may be received by another stethoscope communicating therewith so as to enable co-listening by one or more users of said one and another stethoscopes.

2. An electronic stethoscopy system as in claim 1, wherein said remote unit comprises:

a receiving circuit including a demodulator for demodulating a signal received from one of said plurality of stethoscopes, a deemphasizer for deemphasizing high frequencies and a bandpass filter for passing audible frequencies;

a bandpass filter bank for dividing a signal received from said receiving circuit into several audio bands and of respectively transforming each signal of each audio band into a digital signal representing energy of that band at a certain time, said bandpass filter bank including a plurality of narrow-band filters for extracting a certain frequency component from the received signal as an audio band, a plurality of full-wave retifiers for transforming said audio bands into d.c. signals, a plurality of lowpass filters for filtering out high frequency noise in said d.c. signals, and a plurality of A/D converters for converting said filtered d.c. signals into digital signals, whereby a continuous received signal can be expressed as discrete parameters from each audio band at discrete time intervals;

means connected to said receiving circuit for detecting the rate of the signal waveform of said received signal;

processing means for receiving the discrete parameters from said bandpass filter bank and an output of said rate detecting means for forming a pattern from the discrete parameters, comparing said formed pattern with other predetermined patterns representative of particular symptoms, and storing said formed and predetermined patterns in a data base along with criteria for pattern comparison; and output and transmitting means for outputting said formed pattern or other symptom-related data outputted by said processing means in accordance with said comparison, including a D/A converter and an amplifier for converting the output of said processing means into an analog signal and amplifying said analog signal, and an emphasizer and a modulator for respectively emphasizing high frequencies of said analog signal and then modulating said analog signal for transmission.

3. An electronic stethoscopy system as in claim 2, wherein each of said stethoscopes further includes a control-signal generator for generating several different signals selected by a switch set, and a third switch for seletively connecting said control signals or said amplified and filtered signal from said pick-up circuit to said transmitting circuit of said stethoscope, said control signals including signals for controlling said processing means of said remote unit and for selecting predetermined data stored in said data base.

* * * * *

UNITED STATES PATENT AND TRADEMARK OFFICE
CERTIFICATE OF CORRECTION

PATENT NO. : 4,770,189

DATED : September 13, 1988

INVENTOR(S) : SHYU, Jia-Ming

It is certified that error appears in the above-identified patent and that said Letters Patent is hereby corrected as shown below:

ON THE FIRST INFORMATION PAGE:

Please read:

"[75] Inventor: Jia-Ming Shyu, Hsien, Taiwan" as

--[75] Inventor: Jia-Ming Shyu, Hsin Chu Hsien, Taiwan--.

IN THE DRAWINGS:

FIG. 3, please read in --DEMODULATOR-- with a connecting line to No. "10".

FIG. 4, please read in a connecting line between "DEEMPHASIZER" and No. "23" and "RECORDER" and No. "40";

please read in --PICKUP-- after "SIGNAL CHARACTERISTIC" at No. "31";

please read --BASE-- instead of "PHASE" after "DATA" at No. "34"; and read "DIGITOL" as --DIGITAL--.

IN THE SPECIFICATION:

Column 3, line 27, read "stetoscopes" as --stethoscopes--;
      line 36, read "S4" as --set (S4)--;
         line 48, read "S4" as --(S4)--.

UNITED STATES PATENT AND TRADEMARK OFFICE
CERTIFICATE OF CORRECTION

PATENT NO. : 4,770,189
DATED : September 13, 1988
INVENTOR(S) : SHYU, Jia-Ming

It is certified that error appears in the above-identified patent and that said Letters Patent is hereby corrected as shown below:

Column 6, line 61, read "retifiers" as --rectifiers--.

Signed and Sealed this

Ninth Day of May, 1989

Attest:

DONALD J. QUIGG

*Attesting Officer*     Commissioner of Patents and Trademarks